(12) United States Patent
Park et al.

(10) Patent No.: US 8,951,554 B2
(45) Date of Patent: Feb. 10, 2015

(54) MICROCAPSULE, STRUCTURE HAVING A MICROCAPSULE, ARTICLE HAVING A MICROCAPSULE, AND METHOD OF PREPARING MICROCAPSULES

(75) Inventors: Jong-jin Park, Yongin-si (KR); Jong-min Kim, Suwon-si (KR); Sung-ho Jin, San Diego, CA (US)

(73) Assignee: Samsung Electronics Co., Ltd., Gyeonggi-Do (KR)

( * ) Notice: Subject to any disclaimer, the term of this patent is extended or adjusted under 35 U.S.C. 154(b) by 927 days.

(21) Appl. No.: 12/457,235

(22) Filed: Jun. 4, 2009

(65) Prior Publication Data
US 2010/0112018 A1  May 6, 2010

(30) Foreign Application Priority Data
Oct. 31, 2008 (KR) .................... 10-2008-0107969

(51) Int. Cl.
| | | |
|---|---|---|
| *A61K 8/11* | (2006.01) | |
| *A61K 8/27* | (2006.01) | |
| *A61K 8/29* | (2006.01) | |
| *A61K 8/19* | (2006.01) | |
| *A61K 8/28* | (2006.01) | |
| *A61K 8/73* | (2006.01) | |
| *A61K 9/50* | (2006.01) | |
| *A61K 9/00* | (2006.01) | |
| *A61Q 13/00* | (2006.01) | |
| *A61Q 15/00* | (2006.01) | |
| *C01G 23/00* | (2006.01) | |
| *C01G 49/00* | (2006.01) | |
| *C01G 49/06* | (2006.01) | |
| *C01G 51/00* | (2006.01) | |
| *C01G 53/00* | (2006.01) | |
| *H01F 1/28* | (2006.01) | |
| *H01F 1/34* | (2006.01) | |
| *H01F 1/36* | (2006.01) | |

(52) U.S. Cl.
CPC .................. *A61K 9/0009* (2013.01); *A61K 8/11* (2013.01); *A61K 8/19* (2013.01); *A61K 9/5094* (2013.01); *A61Q 13/00* (2013.01); *A61Q 15/00* (2013.01); *C01G 23/006* (2013.01); *C01G 49/0063* (2013.01); *C01G 49/0072* (2013.01); *C01G 49/06* (2013.01); *C01G 51/00* (2013.01); *C01G 53/00* (2013.01); *C01G 53/006* (2013.01); *H01F 1/28* (2013.01); *H01F 1/344* (2013.01); *H01F 1/36* (2013.01); *A61K 2800/412* (2013.01); *A61K 2800/47* (2013.01); *A61K 2800/56* (2013.01); *C01P 2002/54* (2013.01); *C01P 2004/51* (2013.01); *C01P 2004/61* (2013.01); *C01P 2006/16* (2013.01); *C01P 2006/42* (2013.01)

USPC .......... 424/451; 424/501; 424/489; 424/497; 424/493; 424/494

(58) Field of Classification Search
CPC .................. A61K 2800/645; A61K 2800/651; A61K 2800/56; A61K 2800/47; A61K 2800/412; A61K 2201/04; A61K 2201/034; A61K 2008/115; A61K 8/19; A61K 8/11; A61K 8/25; A61K 8/27; A61K 8/28; A61K 8/29; A61K 8/731; A61K 9/5005; A61K 9/50; A61K 9/501; A61K 9/5021; A61K 9/5036; A61K 9/5042; A61K 9/5094; A61K 47/36; A61K 47/38
USPC .................. 424/451, 501, 489, 497, 493, 494
See application file for complete search history.

(56) References Cited

U.S. PATENT DOCUMENTS

| | | | | |
|---|---|---|---|---|
| 3,790,497 | A | * | 2/1974 | Sato et al. .................. 264/4.3 |
| 4,268,411 | A | * | 5/1981 | Iwata et al. ................ 428/402.2 |
| 4,847,007 | A | * | 7/1989 | Queiser et al. .................. 366/75 |
| 5,411,398 | A | | 5/1995 | Nakanishi et al. |
| 5,574,372 | A | | 11/1996 | Moritz et al. |
| 5,834,121 | A | * | 11/1998 | Sucholeiki et al. ........... 428/407 |
| 6,106,946 | A | | 8/2000 | Tanaka et al. |
| 6,238,650 | B1 | | 5/2001 | Lapidot et al. |
| 6,299,972 | B1 | | 10/2001 | Iwasaki et al. |
| 6,599,234 | B1 | | 7/2003 | Gray et al. |
| 6,727,881 | B1 | | 4/2004 | Albert et al. |
| 6,738,050 | B2 | | 5/2004 | Comiskey et al. |
| 6,870,661 | B2 | | 3/2005 | Pullen et al. |
| 6,876,143 | B2 | | 4/2005 | Daniels |
| 6,881,776 | B2 | | 4/2005 | Butuc |
| 6,927,201 | B2 | * | 8/2005 | Hsu et al. ...................... 510/441 |
| 7,027,030 | B2 | | 4/2006 | Kanno |
| 7,279,064 | B2 | | 10/2007 | Daniel et al. |
| 7,309,500 | B2 | | 12/2007 | Kim et al. |

(Continued)

FOREIGN PATENT DOCUMENTS

| | | |
|---|---|---|
| EP | 1923423 | 5/2008 |
| KR | 10-2008-0059380 | 6/2008 |
| WO | WO 2013/027219 A1 * | 2/2013 |

OTHER PUBLICATIONS

Incipient defintion (Merriam-Webster Dictionary, http://www.merriam-webster.com/dictionary/incipient, 1 page, accessed on Nov. 15, 2013).*

*Primary Examiner* — Johann R Richter
*Assistant Examiner* — Alma Pipic
(74) *Attorney, Agent, or Firm* — Harness, Dickey & Pierce, P.L.C.

(57) ABSTRACT

A microcapsule, a structure including a microcapsule, an article including a microcapsule and a method of preparing microcapsules provided, the microcapsule includes at least one material selected from the group consisting of a magnetic substance, a dielectric substance and a combination thereof. The microcapsule also includes a volatile material.

19 Claims, 2 Drawing Sheets

(56) References Cited

U.S. PATENT DOCUMENTS

| | | |
|---|---|---|
| 7,622,132 B2 * | 11/2009 | Lee et al. .................. 424/401 |
| 2003/0108733 A1 | 6/2003 | Bossert |
| 2004/0014860 A1 * | 1/2004 | Meier et al. ............... 524/394 |
| 2005/0193758 A1 * | 9/2005 | Wells ........................ 62/324.2 |
| 2008/0164960 A1 | 7/2008 | Schnell et al. |
| 2008/0164963 A1 | 7/2008 | Tominaga et al. |
| 2008/0180308 A1 | 7/2008 | Okada et al. |
| 2008/0311064 A1 * | 12/2008 | Lei et al. .................. 424/70.11 |

* cited by examiner

MICROCAPSULE, STRUCTURE HAVING A MICROCAPSULE, ARTICLE HAVING A MICROCAPSULE, AND METHOD OF PREPARING MICROCAPSULES

CROSS-REFERENCE TO RELATED APPLICATIONS

This application claims the benefit of priority under 35 U.S.C. §119 from Korean Patent Application No. 10-2008-0107969, filed on Oct. 31, 2008 in the Korean Intellectual Property Office, the disclosure of which is incorporated herein in its entirety by reference.

BACKGROUND

1. Field

Example embodiments relate to a microcapsule, a structure including a microcapsule, an article including a microcapsule and a method of preparing microcapsules.

2. Description of the Related Art

A microcapsule is a particle having a particle diameter of about 50-nm to about 2000-μm. The microcapsule contains an incipient and an excipient protecting the incipient. The microcapsule may be used for various purposes (e.g., protection of an incipient that is sensitive to external factors, drug delivery, emission of perfume, agrichemicals, etc).

For example, an emission time of the incipient contained in the microcapsule may be controlled by forming the excipient of the microcapsule from a material that dissolves, not in an acid material, but in a basic material.

SUMMARY

Example embodiments relate to a microcapsule, a structure including a microcapsule, an article including a microcapsule and a method of preparing microcapsules.

The microcapsule according to example embodiments includes a volatile material and at least one material selected from the group consisting of a magnetic substance, a dielectric substance and combinations thereof.

Other example embodiments include a structure having at least one material selected from the group consisting of the above microcapsule and an incipient. The structure also includes a porous material having the at least one material received therein.

Yet other example embodiments include an article including the above microcapsule or the structure.

The method of preparing a plurality of microcapsules according to example embodiments includes preparing an emulsified solution by adding an incipient into a solution, in which a polymer is dissolved and which is immiscible with the incipient, and agitating the emulsified solution. Hardened microcapsules, which are dispersed in the emulsified solution, may be prepared by adding a hardener into the emulsified solution and agitating the dispersion. The hardened microcapsules may be separated from the dispersion.

BRIEF DESCRIPTION OF THE DRAWINGS

The patent or application file contains at least one drawing executed in color. Copies of this patent or patent application publication with color drawing will be provided by the Office upon request and payment of the necessary fee.

These and/or other aspects will become apparent and more readily appreciated from the following description of the embodiments, taken in conjunction with the accompanying drawings of which.

DETAILED DESCRIPTION

Figure 1:
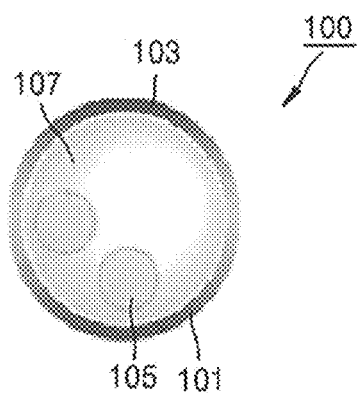
FIG. 1 is a schematic diagram illustrating a microcapsule according to example embodiments.

Various example embodiments will now be described more fully with reference to the accompanying drawings in which some example embodiments are shown. However, specific structural and functional details disclosed herein are merely representative for purposes of describing example embodiments. Thus, the invention may be embodied in many alternate forms and should not be construed as limited to only example embodiments set forth herein. Therefore, it should be understood that there is no intent to limit example embodiments to the particular forms disclosed, but on the contrary, example embodiments are to cover all modifications, equivalents, and alternatives falling within the scope of the invention.

In the drawings, the thicknesses of layers and regions may be exaggerated for clarity, and like numbers refer to like elements throughout the description of the figures.

Although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term "and/or" includes any and all combinations of one or more of the associated listed items.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including," if used herein, specify the presence of stated features, integers, steps, operations, elements and/or components, but do not preclude the presence or addition of one or more other features, integers, steps, operations, elements, components and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In order to more specifically describe example embodiments, various aspects will be described in detail with reference to the attached drawings. However, the present invention is not limited to example embodiments described.

Example embodiments relate to a microcapsule, a structure including a microcapsule, an article including a microcapsule and a method of preparing microcapsules.

According to example embodiments, a microcapsule includes a volatile material and at least one material selected from the group consisting of a magnetic substance, a dielectric substance, an electromagnetic substance and combinations thereof. The microcapsule may be spherical, but is not limited thereto. The microcapsule may also have other shapes (e.g., a rod shape, an oval shape, or the like).

The at least one material may vibrate in response to electromagnetic wave irradiation. The vibration energy is converted into thermal energy. The volatile material is volatilized due to the thermal energy. The irradiated electromagnetic waves may be radio waves in a frequency range of about 3-Hz to about 300-GHz. Other materials, which vibrate if irradiated by electromagnetic waves, convert the vibration energy into thermal energy and emit the thermal energy, may be included in the microcapsule.

The microcapsule may expand due to the application of heat. The volatile material may be emitted outside the microcapsule if the microcapsule expands.

The particle diameter of the at least one material (i.e., the magnetic substance, the dielectric substance and/or the electromagnetic substance) may be about 10-nm to about 10000-nm. For example, the particle diameter of the at least one material may be about 50-nm to about 200-nm. Nanoparticles, nanorods and the like may be used as the at least one material.

The particle diameter of the microcapsule may be about 50-nm to about 2000-μm. For example, the particle diameter of the microcapsule may be about 50-nm to about 1000-nm.

The content of the at least one material contained in the microcapsule may be about 0.0001-wt % to about 10-wt % of the total weight of the microcapsule. For example, the content of the at least one material contained in the microcapsule may be about 0.01-wt % to about 2-wt %.

According to other example embodiments, the at least one material may vibrate if irradiated by electromagnetic waves in the range of about 3-Hz to about 300-GHz. Vibration of the at least one material may increase if electromagnetic waves in the above resonance frequency range are irradiated from the outside.

According to example embodiments, the at least one material may have a resonance frequency of about 3-Hz to about 300-GHz. The magnetic substance and/or the dielectric substance may vibrate if irradiated by electromagnetic waves that are in a resonance frequency range that does not exactly correspond to the resonance frequency range of the magnetic substance and/or the dielectric substance.

For example, the frequency of the electromagnetic waves may be in a range of about 300-kHz to about 3000-kHz (Medium Frequency), about 30-MHz to about 300-MHz (Very High Frequency), about 300-MHz to about 3000-MHz (Ultra High Frequency), and about 3-GHz to about 30-GHz (Super High Frequency). As such, it may be easier to control the rate and amount of the volatile material emitted to the outside of the microcapsule by controlling the frequency and power of the electromagnetic waves irradiated to the microcapsule. A volatile material may be volatilized only by thermal energy in a conventional microcapsule. In microcapsules according to example embodiments, both thermal energy and electromagnetic energy may be used.

According to yet other embodiments, the magnetic substance may be a ferromagnetic substance, a ferrimagnetic substance or a combination of these. For example, the magnetic substance may be a metal, a metal alloy, an M-type ferrite, a spinel-type ferrite or a combination thereof. The magnetic substance, for example, may be $\gamma\text{-}Fe_2O_3$, $CrO_2$, $EuO$, $MO\cdot Fe_2O_3$, (wherein M is at least one metal selected from the group consisting of cobalt (Co), nickel (Ni), manganese (Mn), zinc (Zn), cadmium (Cd), Cu—Zn ferrite, Ni—Zn ferrite, $ZnFe_2O_4$ or a combination of these.

According to example embodiments, the dielectric substance may be $Ba_xSr_{1-x}TiO_3$ (wherein 0<x<1) (known as BST or barium strontium titanate), $Ta_2O_5$, $Y_2O_3$, and $TiO_2$, $PbZr_xTi_{1-x}O_3$ (wherein 0<x<1) (known as PZT or plumbum zirconium titanate), $Bi_4Ti_3O_2$, $BaMgF_4$, $SrBi_2(Ta_{1-x}Nb_x)_2O_9$ (wherein 0<x<1), $Ba(Zr_{1-x}Ti_x)O_3$ (wherein 0<x<1) (known as BZT or barium zirconium titanate), $BaTiO_3$, $SrTiO_3$, $Bi_4Ti_3O_{12}$ or a combination of these.

According to example embodiments, the volatile material may emit perfume and/or gas. The volatile material is a material that is volatilized by heat. The volatile material may be an organic compound that exists in a liquid state at room temperature. The volatile material is a material emitting a perfume or gas via volatilization, transmitting signals detectable by olfaction, gustation or other physiological methods of perception. The volatile material may be classified according to the volatilization temperature as a low boiling point volatile material with a volatilization temperature of 100° C. or lower at normal pressure, a middle boiling point volatile material with a volatilization temperature of 100° C. to 150° C. at normal pressure or a high boiling point volatile material with a volatilization temperature of 150° C. or higher at normal pressure.

According to other example embodiments, the volatile material may be nitrous oxide ($N_2O$), a perfume, a deodorant, an anesthetic, an antibiotic substance, a refrigerant, an air cleaning agent, an agrichemical, a medicine or a combination of these. After being volatilized, the deodorant reacts with a compound that causes an unpleasant smell in order to eliminate the unpleasant smell. The anesthetic is a material that induces insensibility of olfaction if volatized. The antibiotic substance is a material that suppresses propagation of bacteria. The refrigerant is a material that absorbs, or extracts heat. The air cleaning agent is a material that cleans the air if volatilized.

Examples of the perfume include both a natural perfume and synthetic perfume, as well as any material that makes a person smell a certain scent. For example, the perfume may include a sea scent, a leaf scent, a food scent (e.g., coffee), a tree scent (e.g., phytoncide), a fruit scent (e.g., lemon and/or strawberry) or a flower scent (e.g., rose and/or vanilla).

FIG. 1 is a schematic diagram illustrating a microcapsule according to example embodiments.

Referring to FIG. 1, a microcapsule 100 may have a core 101 and a shell 103 (collectively referred to as a "core/shell structure"). At least one material 105 and a volatile material 107 may be included in the core 101. For example, a perfume and a magnetic particle may be contained in the core 101 and the shell 103 may be formed outside the core 101. The microcapsule 100 having the core/shell structure may be prepared using any materials and techniques that are well-known in the art. The microcapsule 100 may have other various structures other than the core/shell structure. For example, the microcapsule 100 may have a structure in which incipients are dispersed in a polymer particle without distinguishing the core 101 from the shell 103.

The shell 103 may include a metal, an inorganic compound, an organic compound or combinations thereof. The metal and/or inorganic compound may be contained in, or form, the shell 103 as an aggregate of fine particles. The organic compound may be a polymer. However, example embodiments are not limited thereto. For example, the organic compound may be a compound having a low molecular weight, which is solid or substantially viscous at room temperature.

For example, the shell 103 may include gold, silver, silicon derivatives, thermoplastic resin, thermosetting resin, copolymer, protein, polyphosphate, polysaccharide, Arabia gum, alginate, chitosan, carrageenan, pectin, cellulose, cellulose derivative or a combination of these.

According to example embodiments, the shell 103 may be porous. The volatile material 107 included in the core 101 may be easily emitted.

According to example embodiments, the shell 103 may be expanded by applying heat. If the shell 103 is porous, pores of the porous shell may expand or contract in size as the temperature varies.

A microcapsule according to example embodiments may have various structures.

Figure 2:
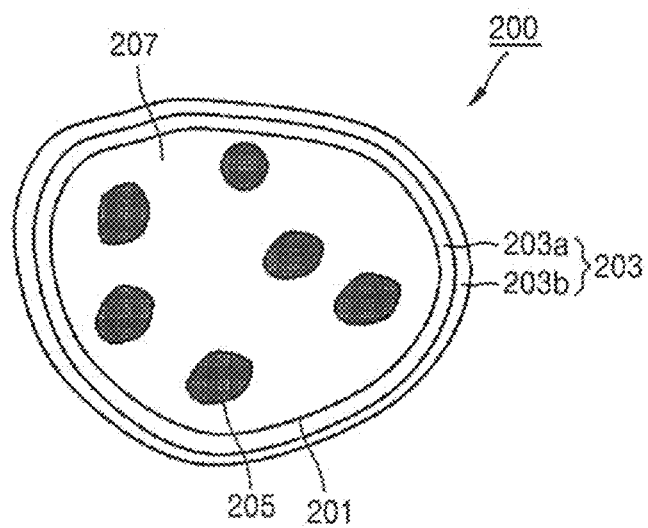
FIG. 2 is a schematic diagram illustrating a microcapsule including a multi-layer shell structure according to example embodiments.

FIG. 2 is a schematic diagram illustrating a microcapsule including a multi-layer shell structure according to example embodiments.

Referring to FIG. 2, a microcapsule 200 may have a shell 203, which has a multi-layer structure. For example, the shell 203 may include a first layer 203a and a second layer 203b. However, example embodiments are not limited thereto. The shell 203 may have more than two layers.

At least one material 205 and a volatile material 207 may be included in a core 201 of the microcapsule 200. If the shell 203 has the multi-layer structure, a concentration of the volatile material 207 (e.g., perfume) with the shell 203 may be controlled.

Figure 3:
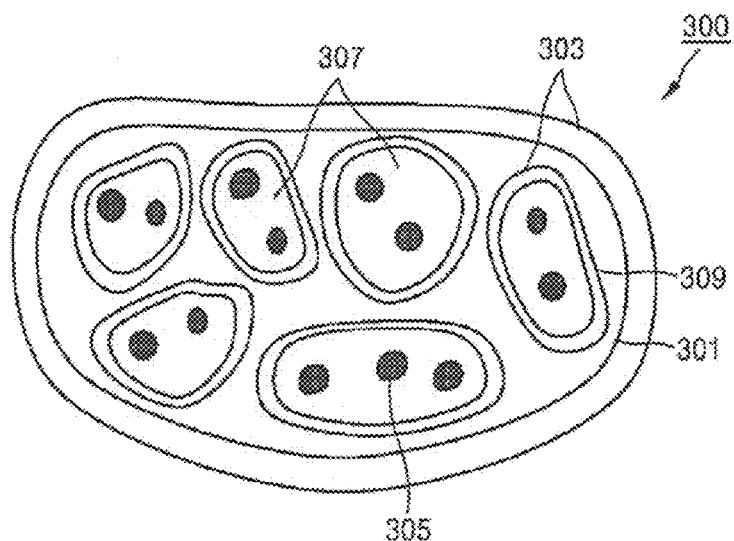
FIG. 3 is a schematic diagram illustrating a microcapsule including a plurality of microparticles in a core of the microcapsule according to example embodiments.

FIG. 3 is a schematic diagram illustrating a microcapsule including a plurality of microparticles in a core of the microcapsule according to example embodiments.

According to example embodiments, a microcapsule 300 may include a plurality of microparticles 309 in a core 301 of the microcapsule 300. The microcapsule 300 may be larger than the microparticles 309. The microparticles 309 may be microcapsules that are smaller than the microcapsule 300. The microparticles 309 may each have a core/shell structure. As such, a plurality of volatile materials 307 may be contained in the microcapsule 300 without being mixed with other materials. For example, if one of the microparticles 309 contained in the core 301 includes at least one material 305 (e.g., a magnetic and/or dielectric substance) that has different resonance frequency than the at least one material 305 in the other microparticles 309, different volatile materials (e.g., perfume or gas) may be selectively emitted by selecting a frequency of electromagnetic waves to be irradiated to the microcapsule 300. The microcapsule 300 and the microparticle 309 may have respective shells 303.

Figure 4:
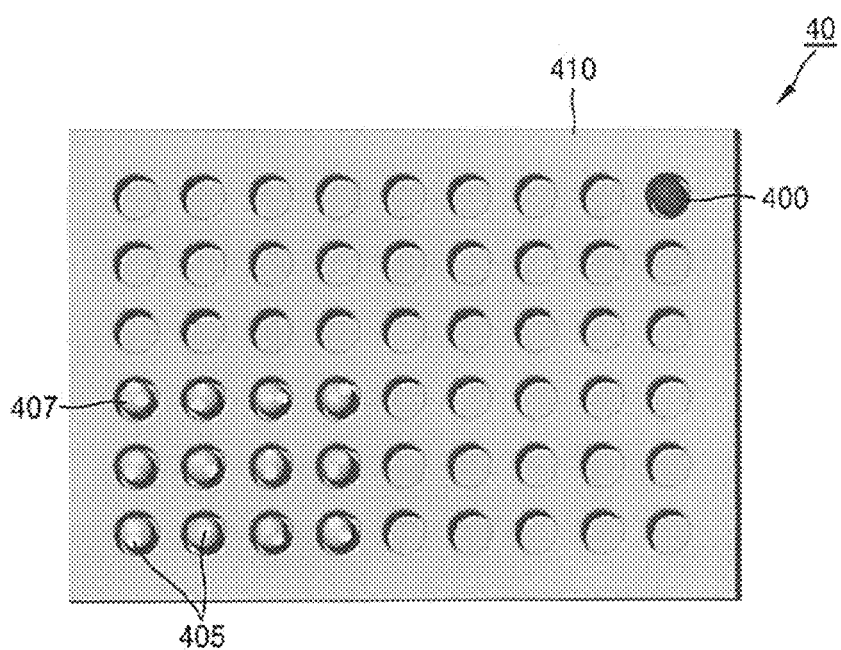
FIG. 4 is a schematic diagram illustrating a structure wherein a porous material includes a plurality of microcapsules received therein and the microcapsules contain at least one magnetic substance imbedded therein according to example embodiments.

FIG. 4 is a schematic diagram illustrating a structure wherein a porous material includes microcapsules received therein and the microcapsules contain magnetic substances imbedded therein according to example embodiments.

Referring to FIG. 4, a structure 40 according to example embodiment includes at least one active material 400 selected from the group consisting of a microcapsule and an incipient. The structure 40 includes a porous material 410 having the at least one active material 400 received therein.

The at least one active material 400 may include a volatile material 407 and at least one material 405 selected from the group consisting of a magnetic substance, a dielectric substance and a combination thereof. The volatile material 407 and the at least one material 405 included in the at least one active material 400 are similar to those previously described in the microcapsules 100, 200 and 300. Therefore, a description thereof will be omitted for the sake of brevity.

The porous material 410 may be a mesoporous material. The mesoporous material may have pores of about 2-nm to about 50-nm in diameter. For example, the mesoporous material may be alumina, silica, niobium oxide, tantalum oxide, zirconium oxide, cerium oxide, tin oxide or combinations thereof.

The porous material 410 is not limited to the mesoporous material. The porous material 410 may be any material that is used in the art, and that accommodates the microcapsule or incipient.

An article according to example embodiments includes a microcapsule and/or a structure as described above. The article is not limited particularly so long as the article includes the microcapsule and/or the structure. The article may include an oscillator emitting electromagnetic waves. Vibration of a magnetic substance and/or a dielectric substance contained in the microcapsule or structure may be induced by the oscillator.

For example, the article may be an electronic apparatus (e.g., a TV, a radio, an MP3 player, a DMB player, a wired/wireless telephone, a game player, a navigator, a liquid crystal display or the like), but is not limited thereto. For example, if a microcapsule or structure according to example embodiments is included in a wireless telephone, a volatile material may be volatilized from the microcapsule (or structure) according to radio waves generated in an oscillator installed in the wireless telephone according to a selected signal. As such, a scent may be selectively emitted from the wireless telephone.

A method of preparing a plurality of microcapsule according to example embodiments includes preparing an emulsified solution by adding incipient(s) into a solution, in which a polymer is dissolved and which is immiscible with the incipient. The emulsified solution may be agitated. Hardened microcapsules, which are dispersed in the emulsified solution, may be prepared by adding a hardener into the emulsified solution and agitating the resulting solution. The hardened microcapsules may be separated from the resulting solution.

For example, perfume and magnetic particles may be added to an aqueous solution of pH 4 to 6 in which a water-soluble polymer is dissolved, and agitated at a high speed of 1000-rpm or greater to prepare an emulsified solution. A melamine solution of pH 8 to 9, to which melamine and formalin are added, is separately prepared. The melamine solution is added to the emulsified solution and agitated at room temperature at a speed of 1000-rpm or greater to stabilize the emulsified solution. The stabilized solution is agitated at a temperature of 50° C. or higher to carry out a cross-linking reaction. Obtained microcapsules are separated and washed.

According to example embodiments, the microcapsule may be manufactured using techniques well-known in the art (e.g., coacervation, interfacial polymerization, solvent evaporation, spray coating, suspension polymerization, emulsion polymerization or the like).

The hardener may be any hardener that is used in the art. Examples of the hardener include melamine, polyhydric alcohol, polyvalent amine, polybasic acid, polyepoxy or combinations thereof. The term 'poly-' regarding the hardener means that at least two reactive functional groups are contained in a molecule.

Examples and comparative examples will now be described more fully. However, the scope of example embodiments is not restricted to the following examples.

Manufacture of a Microcapsule

Example 1

200-g of polypyrrolidone solution (PVP10 available by Aldrich Chemical Company) was charged into a reactor, and the pH of the solution was adjusted (or controlled) to 4.5 to 5. 15-g of strawberry scent and 0.1 g of nano-magnetic particles having an average particle diameter of 10-μm (BM547 BioMag Superparamagnetic Iron Oxide, available by Bangs Laboratories, Inc., U.S.A, Magnetization 25-35 EMU/gram) were added and agitated at 1500-rpm for 20 minutes to prepare an emulsion solution. After mixing 5-g of melamine and 10.28-g of formalin (37% solution) in a separate beaker, triethanol amine was added to control the pH to be pH 8.0 to 8.5, and heated at 60° C. to form a transparent solution. 25-g of water was added to the heated solution to prepare a melamine solution. The melamine solution was added to the emulsified solution at 25° C. The temperature of the melamine solution was raised to 42° C. The solution was agitated at 1500-rpm for 10 minutes so that emulsified particles were stabilized. The temperature of the reactor was raised to 60° C., and the solution was agitated at 250-rpm for 2 hours to carry out a cross-linking reaction. Upon completion of the reaction, particles dispersed in the solution were separated by filtration, and washed with distilled water several times and dried in order to obtain 170-g of microcapsules having a particle diameter distribution of 30-μm to 150-μm.

Example 2

120-g of microcapsules having a particle diameter distribution of 120-nm to 500-nm were obtained using the same method as in Example 1 except that titanium oxide ($TiO_2$) having an average particle diameter distribution of 50-nm was used as dielectric nanoparticles instead of the nano-magnetic particles.

Examination Example 1

Experiment of Emission of a Volatile Material

In a room of 10-$m^2$ that was closed tightly and from which smell was eliminated, 10-g of microcapsules manufactured according to Example 1 were arranged on a glass substrate at a temperature of 20° C. Radio waves having a frequency of 500-Hz were irradiated to the microcapsules using an oscillator. After irradiating the radio waves, the experimenter sensed a strawberry scent.

As described above, emission of a volatile material contained in the a microcapsule may be controlled using radiation of electromagnetic waves according to example embodiments.

The foregoing is illustrative of example embodiments and is not to be construed as limiting thereof. Although a few example embodiments have been described, those skilled in the art will readily appreciate that many modifications are possible in example embodiments without materially departing from the novel teachings and advantages. Accordingly, all such modifications are intended to be included within the scope of this invention as defined in the claims. In the claims, means-plus-function clauses are intended to cover the structures described herein as performing the recited function, and not only structural equivalents but also equivalent structures. Therefore, it is to be understood that the foregoing is illustrative of various example embodiments and is not to be construed as limited to the specific embodiments disclosed, and that modifications to the disclosed embodiments, as well as other embodiments, are intended to be included within the scope of the appended claims.

What is claimed is:

1. A microcapsule, comprising:
a plurality of microparticles each encapsulating,
(i) at least one material selected from the group consisting of a magnetic substance, a dielectric substance and combinations thereof, and
(ii) a volatile material,
wherein the microcapsule has a core encapsulating the plurality of microparticles and a shell surrounding the core,
the shell is formed from a hardener,
the at least one material vibrates in response to electromagnetic waves irradiation whereby vibration energy from the at least one material is converted to thermal energy that is used to vaporize the volatile material,
the shell includes a plurality of pores that expand and contract in response to heat applied to the shell whereby the vaporized volatile material is emitted from the expanded pores when the heat is applied to the shell, and
a first microparticle from among the plurality of microparticles includes a first type of the at least one material that vibrates at a different resonance frequency than a second type of the at least one material included in a second microparticle from among the plurality of microparticles.

2. The microcapsule of claim 1, wherein the magnetic substance or the dielectric substance vibrates if irradiated by magnetic waves of about 3-Hz to about 300-GHz.

3. The microcapsule of claim 1, wherein the magnetic substance is at least one selected from the group consisting of a ferromagnetic substance, a ferrimagnetic substance and combinations thereof.

4. The microcapsule of claim 1, wherein the magnetic substance is at least one selected from the group consisting of a metal, a metal alloy, an M-type ferrite, a spinel-type ferrite and combinations thereof.

5. The microcapsule of claim 1, wherein the magnetic substance is at least one selected from the group consisting of $\gamma$-$Fe_2O_3$, $CrO_2$, $EuO$, $CoO.Fe_2O_3$, $NiO.Fe_2O_3$, $Mn.Fe_2O_3$, $ZnO.Fe_2O_3$, $CdO.Fe_2O_3$, Cu—Zn ferrite, Ni—Zn ferrite, $ZnFe_2O_4$ and combinations thereof.

6. The microcapsule of claim 1, wherein the dielectric substance is at least one selected from the group consisting of $Ba_xSr_{1-x}TiO_3$ wherein $0<x<1$ (BST, barium strontium titanate), $Ta_2O_5$, $Y_2O_3$, $TiO_2$, $PbZr_xTi_{1-x}O_3$ wherein $0<x<1$ (PZT, plumbum zirconium titanate), $Bi_4Ti_3O_{12}$, $BaMgF_4$, $SrBi_2(Ta_{1-x}Nb_x)_2O_9$ wherein $0<x<1$, $Ba(Zr_{1-x}Ti_x)O_3$ wherein $0<x<1$ (BZT, barium zirconium titanate), $BaTiO_3$, $SrTiO_3$, $Bi_4Ti_3O_{12}$ and combinations thereof.

7. The microcapsule of claim 1, wherein the volatile material emits perfume or gas.

8. The microcapsule of claim 1, wherein the volatile material is at least one material selected from the group consisting of nitrous oxide (N$_2$O), a perfume, a deodorant, an anesthetic, an antibiotic substance, a refrigerant, an air cleaning agent, an agrichemical and a medicine.

9. The microcapsule of claim 1, wherein the shell includes at least one selected from the group consisting of a metal, an inorganic compound, an organic compound and combinations thereof.

10. The microcapsule of claim 1, wherein the shell includes at least one selected from the group consisting of gold, silver, thermoplastic resin, thermosetting resin, copolymer, protein, polyphosphate, polysaccharide, Arabia gum, alginate, chitosan, carrageenan, pectin, cellulose, and combinations thereof.

11. The microcapsule of claim 1, wherein the shell has multiple layers.

12. A structure, comprising:
the microcapsule according to claim 1; and
a porous material encapsulating the microcapsule.

13. An article, comprising the microcapsule according to claim 1.

14. An article, comprising the structure according to claim 12.

15. A structure, comprising:
the microcapsule according to claim 1;
a volatile material; and
a porous material encapsulating the microcapsule and the volatile material,
wherein the volatile material is at least one material selected from the group consisting of nitrous oxide (N$_2$O), a perfume, a deodorant, an anesthetic, an antibiotic substance, a refrigerant, an air cleaning agent, an agrichemical and a medicine.

16. The microcapsule of claim 1, wherein the magnetic substance or the dielectric substance has a resonance frequency of about 3-Hz to about 300-GHz.

17. The microcapsule of claim 1, wherein at least one of an amount and a rate of the vaporized volatile material emitted from the expanded pores is controllable by changing at least one of a frequency and power of the electromagnetic waves.

18. The microcapsule of claim 1, wherein
the first microparticle includes a first volatile material, and
the second microparticle includes a second volatile material that is vaporized at a different frequency of the electromagnetic waves than the first volatile material.

19. A device comprising:
a wave generating element; and
a microcapsule, including,
(i) at least one material selected from the group consisting of a magnetic substance, a dielectric substance and combinations thereof, and
(ii) a volatile material, wherein the microcapsule has a core and a shell surrounding the core, the shell is formed from a hardener,
the at least one material vibrates in response to electromagnetic waves irradiation whereby vibration energy from the at least one material is converted to thermal energy that is used to vaporize the volatile material, and
the shell includes a plurality of pores that expand and contract in response to heat applied to the shell whereby the vaporized volatile material is emitted from the expanded pores when the heat is applied to the shell.

* * * * *